United States Patent [19]
Reth et al.

[11] 3,982,439
[45] Sept. 28, 1976

[54] APPARATUS FOR SLOWING HEAD PIECES AND SAMPLES COMING FROM A ROLLING MILL

[75] Inventors: Erich Reth, Duisburg-Buchholz; Karl-Heinz Varwig, Mulheim; Karl-Heinz Backhaus, Rheinhausen, all of Germany

[73] Assignee: Demag Aktiengesellschaft, Duisburg, Germany

[22] Filed: Aug. 22, 1975

[21] Appl. No.: 606,927

[30] Foreign Application Priority Data
Sept. 14, 1974 Germany............................ 2444014

[52] U.S. Cl. ................................. 73/423 R; 193/40
[51] Int. Cl.² .......................................... G01N 1/04
[58] Field of Search .......................... 73/421 R, 423; 193/32 R, 40

[56] References Cited
UNITED STATES PATENTS

| | | |
|---|---|---|
| 3,004,648 | 10/1961 | Walther ................................ 193/40 |
| 3,175,402 | 3/1965 | Higami et al. ......................... 73/423 |
| 3,891,080 | 6/1975 | Neises ................................... 193/32 |

FOREIGN PATENTS OR APPLICATIONS 187,589  2/1964  Sweden ............................. 73/421 R

*Primary Examiner*—S. Clement Swisher
*Attorney, Agent, or Firm*—Mandeville and Schweitzer

[57] ABSTRACT

This invention provides apparatus for slowing down the forward speed of severed head pieces or sample pieces issuing from a rolling mill at rolling mill speed, so that the severed pieces may be removed from the main processing line. This is achieved by providing a separate channel or track which may be switched into and out of the main processing line to receive the severed pieces, with the switching channel being in the form of a loop. Because of this shape, the forward speed of the pieces is reduced rapidly in a switching channel requiring very little space, not only because of its shape, but also because the curved course of the channel increases frictional engagement with the severed pieces, as opposed to a straight switching channel.

6 Claims, 2 Drawing Figures

APPARATUS FOR SLOWING HEAD PIECES AND SAMPLES COMING FROM A ROLLING MILL

STATEMENT OF THE INVENTION

This invention covers an apparatus for decelerating head or sample pieces of bar-shaped rolled material issuing from a rolling mill, with a loop-shaped brake channel in which the material is brought to a near or complete halt from rolling speed.

BACKGROUND OF THE INVENTION

The rolling of the bar-shaped material, e.g. round, flat or square steel, requires the segregation of the head pieces which are not true to gauge. Also, it is necessary to take samples, occasionally, from the running rolled material. As much time and effort is required when taking samples and/or head pieces from material which has already been processed into coils, for example, it is already known to separate head pieces and/or samples from the moving rolled material during the production process with cutters specially constructed for this purpose. The separated pieces of material are segregated from the moving production course by means of deflecting devices, such as switches or similar devices into long switch channel sidings where they slowly come to a halt due to friction. Such channels or flutes, however, are very long and, aside from the enormous demand for space, are very expensive.

The object of the present invention is to provide a means for deceleration of the above type, which achieves rapid deceleration of the severed pieces moving at high speeds with minimum space requirements.

DESCRIPTION OF THE INVENTION

The solution, according to this invention, provides the brake flute or channel in the form of a loop deflecting the head or sample pieces from their original direction of motion into a plane substantially parallel with the original direction of motion. The arriving speed of the severed pieces generates a centrifugal force which increases the frictional engagement of the material to be decelerated with the walls of the channel. Therefore, special brake devices, such as brake shoes or simiar auxiliary devices, are not required.

One advantageous aspect of the invention is that the brake channel or flute consists of individual interchangeable segments, thus making it easy to replace those brakes segments which are particularly subject to wear and tear, and particularly those segments arranged near the inlet. In accordance with this invention, furthermore, each brake segment has brake surfaces accommodating round, square and flat profiles, which are arranged side by side and at right angle to the direction of motion of the material to be braked received in the channel. Thus, all profiles, as programmed, may be received in the channel comprised of a plurality of segments, each one of which is profiled to accommodate head pieces or sample pieces of differing geometric configuration in cross section.

In order to bring the brake flute or channel into its effective position, provision is made to displace the brake flute or channel laterally with respect to movement of materials through the rolling line. This provision also makes it possible to remove the brake device completely from the direction of motion of the material and to guide head or sample pieces directly into a subsequent conveyor at low speed. Preferably, the inlet of the brake flute is funnel-shaped. Also, in order to remove head or sample pieces which have come to a stop within the brake channel, there is provided one or more drive elements for moving the pieces slowly out of the channel and onto a conveyor for subsequent handling. The brake segments and/or brake surfaces are made, preferably, of gray cast iron.

With the foregoing and additional objects in view, this invention will now be described in more detail, and other objects and advantages will be apparent from the following description, the accompanying drawings, and the appended claims. As purely illustrative of apparatus which may be used for carrying out this invention, one may note the attached drawings in which a loopshaped brake flute is shown.

DETAILED DESCRIPTION OF PREFERRED EMBODIMENT

Figure 1:
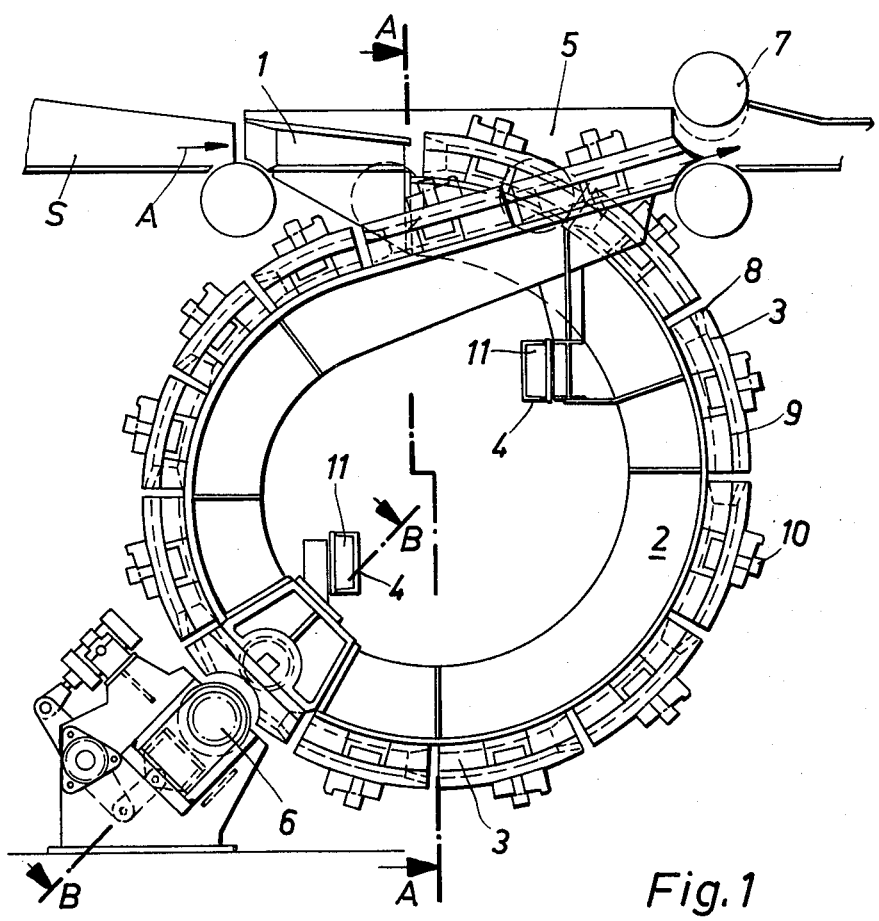
FIG. 1 is a vertical side elevational view in section of apparatus embodying and for practicing the inventon.
Figure 2:
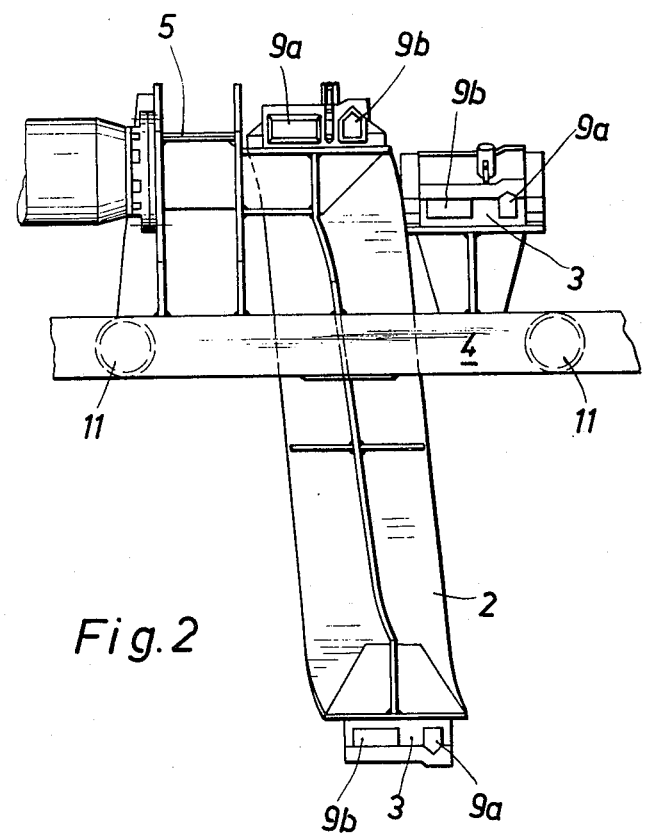
FIG. 2 is a cross section taken along lines A—A of FIG. 1.

Referring to the drawings, in which like reference characters refer to like parts throughout the several views thereof, in FIg. 1, 1 is the funnel-shaped opening for receiving the head or sample pieces S moving in the direction of arrow A, and 5 is the main conveyor for the processing line. Brake loop 2 may be comprised of individual segments 3. The brake surfaces of brake channel 2 are indicated at 9. At the inlet of channel 2, brake surfaces 9 are bevelled, as shown, at 8. Brake segments 3 may be held onto the frame of channel 2 by appropriate means, such as bolts 10. 6 and 7 indicate drive elements for removing any remaining head pieces or samples S from channel 2. The runways or tracks on which the brake flute 2 may be displaced laterally at right angle to main conveyor 5, are indicated at 4. They act as a guide for supporting wheels 11 running on it. In FIG. 2, 9b indicates the brake surfaces for flat and square profile pieces, and 9a those for round profile.

In operation, the head and sample pieces S to be decelerated enter into funnel 1 and are guided to brake flute 2. Due to centrifugal force, head and sample pieces S are pressed against brake surfaces 9. Thus, they are slowed down due to the frictional engagement. Brake channel or flute 2 is displaced laterally at right angles to the direction of movement, so that either round profiled pieces are brought into alignment with brake surface 9a, or flat and square profiled pieces, respectively, with brake surface 9b. Displacement is effected on wheels 11 running on the tracks 4. In the case of head or sample pieces which, due to their low arrival speed, do not require any particular deceleration, brake flute 2 is displaced out of alignment, so that moving conveyor 5 transfers the material further along in the line without engagement with flute 2. Head and sample pieces which do not run the entire length of the brake channel on their own, are moved out by drive element 6 and guided onto the moving conveyor by drive element 7.

While the apparatus herein disclosed forms preferred embodiments of this invention, this invention is not limited to those specific forms of apparatus, and changes can be made therein without departing from the scope of the invention, which is defined in the appended claims.

We claim:
1. Apparatus for decelerating the forward speed of head or sample pieces of bar-shaped rolled material, and having a brake flute in which the material to be decelerated is brought to a near or complete halt from rolling speed, characterized by
   a. said brake flute is configured in the shape of a loop for deflecting said head or sample pieces from their original path of movement into planes substantially parallel with that original path of movement, said flute being positioned substantially parallel to said path; and
   b. means for moving said flute laterally into and out of said path.
2. Apparatus according to claim 1, further characterized by
   a. a plurality of individual interchangeable brake segments; and
   b. said segments being connected together to form said flute.
3. Apparatus according to claim 2, further characterized by
   a. each brake segment being comprised of selectively a brake surface for receiving round, and square or flat profile pieces; and
   b. said round profile receiving surface and said square and flat receiving surface in each segment being positioned side by side, in the direction of lateral movement of said flute.
4. Apparatus according to claim 1, further characterized by
   a. the entrance to said flute being funnel-shaped.
5. Apparatus according to claim 1, further characterized by
   a. drive means in said flute for moving pieces received therein through said flute.
6. Apparatus according to claim 2, further characterized by
   a. the braking surfaces of said plurality of segments being comprised of gray cast iron.

* * * * *